(12) United States Patent
Reynolds

(10) Patent No.: US 8,062,294 B2
(45) Date of Patent: Nov. 22, 2011

(54) IMPLANT WITH INTEGRAL FASTENER RETENTION

(75) Inventor: Joseph Reynolds, Cincinnati, OH (US)

(73) Assignee: Spineform LLC, Cincinnati, OH (US)

( * ) Notice: Subject to any disclaimer, the term of this patent is extended or adjusted under 35 U.S.C. 154(b) by 1142 days.

(21) Appl. No.: 11/227,820

(22) Filed: Sep. 15, 2005

(65) Prior Publication Data

US 2007/0073297 A1 Mar. 29, 2007

(51) Int. Cl.
*A61B 17/56* (2006.01)
(52) U.S. Cl. .......................... 606/60; 606/280; 606/301
(58) Field of Classification Search .............. 606/60–61, 606/69, 72–73, 75, 289, 290, 266–272; 411/354, 411/355, 356
See application file for complete search history.

(56) References Cited

U.S. PATENT DOCUMENTS

| | | | | |
|---|---|---|---|---|
| 4,794,916 A | | 1/1989 | Porterfield et al. ............. 128/78 |
| 5,275,601 A | * | 1/1994 | Gogolewski et al. ......... 606/291 |
| 5,531,554 A | * | 7/1996 | Jeanson et al. ................. 411/399 |
| 5,531,746 A | | 7/1996 | Errico et al. .................... 606/61 |
| 5,578,034 A | | 11/1996 | Estes ............................... 606/61 |
| 5,607,426 A | | 3/1997 | Ralph et al. ..................... 606/61 |
| 5,876,402 A | | 3/1999 | Errico et al. .................... 606/61 |
| 5,954,722 A | * | 9/1999 | Bono ............................... 606/61 |
| 6,139,550 A | | 10/2000 | Michelson ....................... 606/69 |
| 6,193,721 B1 | | 2/2001 | Michelson ....................... 606/70 |
| 6,235,034 B1 | | 5/2001 | Bray ............................... 606/71 |
| 6,322,562 B1 | * | 11/2001 | Wolter ............................ 606/62 |
| 6,342,055 B1 | | 1/2002 | Eisermann et al. |
| 6,527,776 B1 | | 3/2003 | Michelson ....................... 606/70 |
| 6,599,290 B2 | | 7/2003 | Bailey et al. ..................... 606/69 |
| 6,602,255 B1 | | 8/2003 | Campbell et al. ............... 606/69 |
| 6,656,181 B2 | | 12/2003 | Dixon et al. .................... 606/69 |
| 6,695,845 B2 | | 2/2004 | Dixon et al. .................... 606/70 |
| 6,695,846 B2 | | 2/2004 | Richelsoph et al. ............ 606/71 |
| 6,746,450 B1 | * | 6/2004 | Wall et al. ....................... 606/61 |
| 6,793,658 B2 | | 9/2004 | LeHuec et al. |
| 7,229,442 B2 | | 6/2007 | Schafer et al. |
| 2003/0187440 A1 | | 10/2003 | Richelsoph et al. ............ 606/61 |

(Continued)

FOREIGN PATENT DOCUMENTS

WO   WO 2004026159 A1 *   4/2004

(Continued)

*Primary Examiner* — Eduardo C Robert
*Assistant Examiner* — Stuart S Bray
(74) *Attorney, Agent, or Firm* — Gifford, Krass, Sprinkle, Anderson & Citkowski, P.C.

(57) ABSTRACT

An orthopaedic implant provides a simple yet effective retention system requiring no additional components beyond the implant and the associated fastener(s). A plurality of anti-rotation protrusions on the fastener or screw head that match recesses in the implant. The protrusions engage the recesses to prevent the fastener from reversing direction, thereby assuring that the associated fastener does not backout during normal motion of the spine and other anatomical structures. A land on the fastener screw thread assures the fastener will not disengage from the implant should it strip out of the bone. Preventing the fastener from backing out assures it will not detach from the implant or staple, assuring that the implant will remain in place until all fasteners in the system have catastrophically failed. The anti-backout features of the invention provide feedback as they engage, allowing the surgeon to move quickly when placing a fastener without the concern for inadvertent over-tightening. Although ideally suited to a spinal correction system such as a cervical plate, the invention is applicable to other orthopedic devices, including plates and staples for other applications.

10 Claims, 3 Drawing Sheets

U.S. PATENT DOCUMENTS

| | | |
|---|---|---|
| 2003/0187442 A1 | 10/2003 | Richelsoph et al. ............ 606/70 |
| 2004/0097935 A1 | 5/2004 | Richelsoph et al. ............ 606/61 |
| 2004/0172022 A1* | 9/2004 | Landry et al. ................... 606/61 |
| 2005/0059971 A1 | 3/2005 | Michelson ....................... 606/69 |
| 2005/0096657 A1* | 5/2005 | Autericque et al. ............ 606/69 |
| 2005/0137597 A1 | 6/2005 | Butler et al. |
| 2005/0165400 A1* | 7/2005 | Fernandez ...................... 606/69 |
| 2005/0182404 A1 | 8/2005 | Lauryssen et al. |
| 2006/0142766 A1* | 6/2006 | Schafer ........................... 606/69 |

FOREIGN PATENT DOCUMENTS

| | | |
|---|---|---|
| WO | WO-2005062900 | 7/2005 |

\* cited by examiner

IMPLANT WITH INTEGRAL FASTENER RETENTION

FIELD OF THE INVENTION

This invention relates generally to orthopaedic implants and, in particular, to a bone plate having fastener retention features.

BACKGROUND OF THE INVENTION

Hemiepiphysiodesis systems are used for the correction, arresting or slowing of abnormal curvature of the spine, including scoliosis, hyperlordosis and hypokyphosis. Such spinal correction systems bridge vertebra that remain active. However, since the vertebral bodies are still in motion, a gradual dislodgment or outward movement of the fastener could result. As with vertebral plates, partial protrusion of one or more fasteners could damage surrounding structures such as the lung (or the esophagus for cervical plate) and, in a worst case scenario, could permit the plate or correction system to dislodge.

Vertebral (e.g. cervical) plates and other spinal correction systems using hemiepiphysiodesis principles and fastener retention are known in the art. U.S. Pat. No. 6,746,450 to Wall et al., for example, discloses a system that includes a bridge member, a pair of spaced apart barbed legs extending substantially perpendicularly therefrom, and a fastener retaining portion extending substantially longitudinally from each end of the bridge member. The fastener retaining portions are adapted to lie in adjoining relationship when two or more spinal correction systems are arranged in end-to-end abutting relationship. The spinal correction system is intended to correct or arrest scoliosis in a growing spine by spanning the endplate growth centers of adjacent vertebrae, on the convex side of the malformed spine, to retard growth of that side of the spine while permitting unrestrained growth of the concave side of the spine.

Other Fastener Retention features are disclosed in U.S. Pat. No. to 4,794,916 Wolter, which teaches a plate to cover the fastener head to prevent back out. Other patents and applications that cover the fastener head to retain the fastener include U.S. Pat. No. 6,602,255 to Campbell; U.S. Pat. No. 6,599,290 to Bailey; U.S. Pat. Nos. 6,527,776, 6,193,721, 6,139,550 and 2005/059971 to Michelson; U.S. Pat. No. 6,235,034 to Bray; U.S. Pat. No. 5,954,722 to Bono; U.S. Pat. Nos. 5,876,402, 5,531,746 Errico et al. and U.S. Pat. No. 5,607,426 to Ralph et al. All use some type of cover, cap or set screw to cover or affix the fastener by totally or partially covering the screw head. U.S. Pat. No. 5,578,034 uses a snap-ring collar that captures the screw as it passes through it. The collar is made of a shape memory material that locks after placement. U.S. Pat. Nos. 6,656,181 and 6,695,845 to Dixion et al. uses a tapered pin that yields the plate such that frictional force holds the screw and pin together. U.S. Pat. No. 6,695,846 and published application Nos. 2003/0187440, 2003/0187442, 2003/0187440, and 2004/0097935 to Richelsoph et al. disclose a snap-ring-like collar or movable collar that retains the fastener.

It is desirable to install vertebral plates and spinal corrective systems (implants), including the fasteners, endoscopicly. However, endoscopic installation requires good visibility, accurate placement and, perhaps most importantly, no additional steps or components associated with installation. For example, actuation of a fastener retention system as a separate step after installation of the fastener is not desirable. Such added steps consume valuable and expensive time, requiring the patient to remain under general anesthesia longer adding to the procedural risk. Accordingly, a simple and easy to install fastener retention system and method is needed to reduce the complexity and cost of spinal correction.

SUMMARY OF THE INVENTION

This invention improves upon existing orthopaedic correction systems by providing an implant with a simple yet effective retention system requiring no additional components beyond the implant and the associated fastener(s). The preferred embodiment includes a plurality of anti-rotation protrusions on the fastener or screw head that match recesses in the implant. Alternatively, the protrusions may be provided on the implant and the corresponding recesses on the fastener or screw head. In any case, protrusions engage the recesses to prevent the fastener from reversing direction, thereby assuring that the associated fastener does not backout during normal motion of the spine and other anatomical structures.

Although ideally suited to a spinal correction system such as a cervical plate, the invention is applicable to other orthopedic devices, including plates and staples for other applications. Also included is a land on the fastener screw thread that assures the fastener will not disengage from the implant should it strip out of the bone. Preventing the fastener from backing out assures it will not detach from the implant or staple, assuring that the implant will remain in place until all fasteners in the system have catastrophically failed. Such a catastrophic failure of all the fasteners in implant systems is unusual but possible The anti-backout features of the invention provide feedback as they engage, allowing the surgeon to move quickly when placing a fastener without the concern for inadvertent over-tightening. As the protrusions engage, the surgeon feels the engagement as an increase in torque and an immediate drop-off of torque as the protrusions exit one detent and enter another. The toque feedback increases in intensity as the fastener is tightened and it becomes more difficult for the protrusion to ramp up and over each detent.

The tactile-feed-back may be sensed using either a manual screwdriver or a powered driver. Manual and powered screw drives that capture the screw and hold it for endoscopic placement are well known in the art and can also be utilized with the invention.

DETAILED DESCRIPTION OF THE INVENTION

Figure 1:
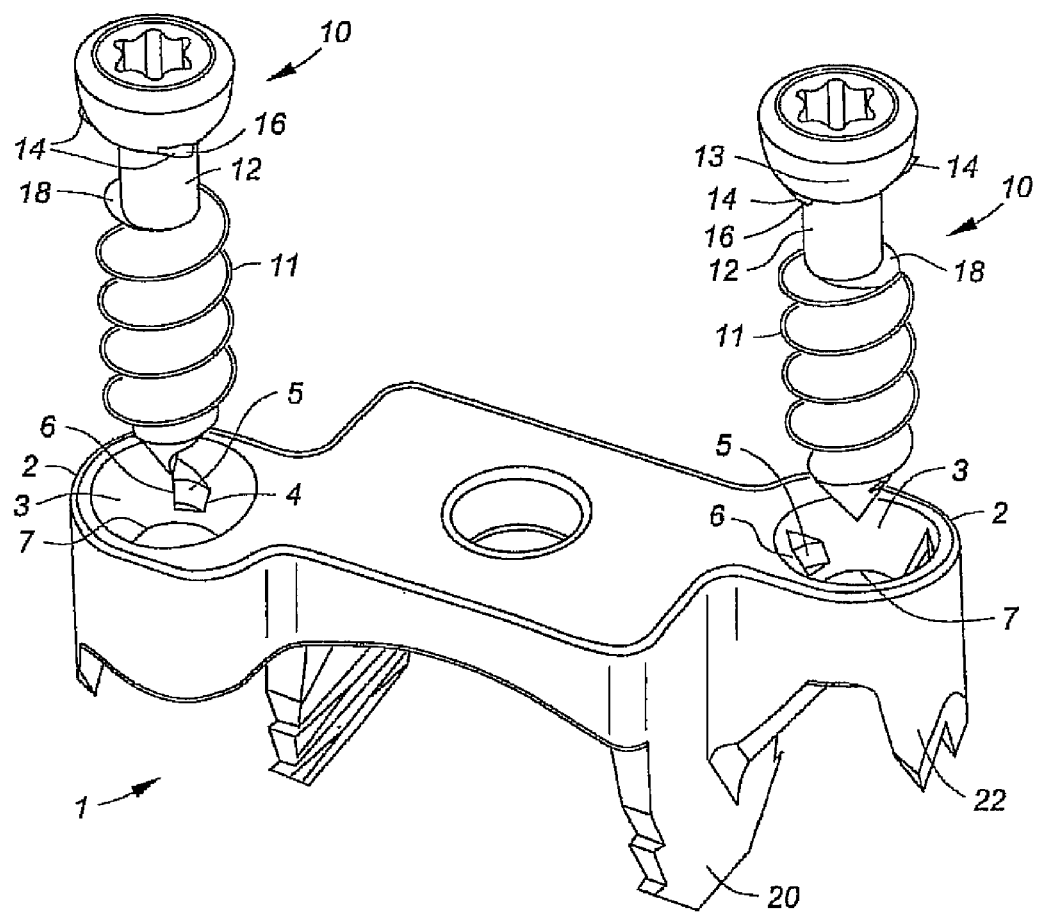
FIG. 1 is an oblique drawing of an implant according to the invention.

Referring now to the drawings, FIG. 1 shows the implant (1) having a top surface and a bottom surface with optional barbed, bone-engaging legs (20) pointed sections (22). The implant includes one or more fastener-retaining portions (2) with fastener retaining bores or holes (7). The holes include flared walls where they emerge from the top surface of the implant. In the preferred embodiment, the walls define a hemispherical fastener contact surfaces (3). The surfaces further include one or more recesses (4) having a ramp-like surface (5) and a stop-surface (6).

Figure 5:
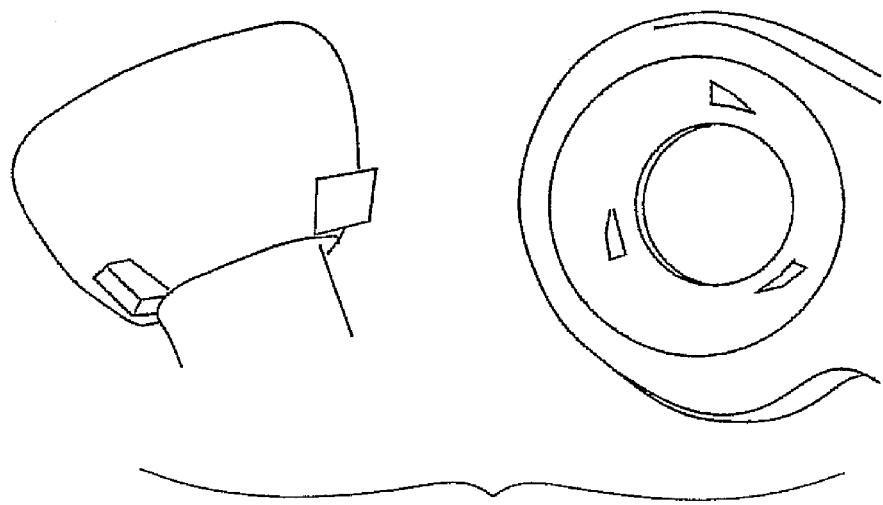
FIG. 5 is an oblique drawing that shows three projections and three recesses.

One or more fasteners (10) each have a thread (11) and screw thread relief (12) that creates a land (18). The fastener has an outer surface (13) that cooperates with the fastener contact surface in the hole (7) in the retaining portions (2) of the implant (1). Again, the outer surface is preferably hemispherical. Though other combinations may be used, in the preferred embodiment the system uses three projections in conjunction with three equally spaced recesses, as shown in FIG. 5.

Located on the spherical head surface are one or more protrusions (14). Each protrusion (14) has a ramp like surface (15) and stop surface (16). When fastener (10) is screwed into hole (7), it cuts into the side of the hole, cutting or deforming a helical path, just as a tap would cut a screw thread in a hole or a sheet metal screw would form an internal thread. Alternatively the hole can be pre-tapped to increase the ease of installation. As a further alternative, the implant may be partially tapped to assure reliable starting of the thread and the fastener would self-tap the remaining portion of the hole. When the fastener (10) reaches the relief (12) in the shaft of the fastener, the fastener (10) can rotate without translating, allowing the fastener to pull the implant down to the surface of the bone.

Figure 2:
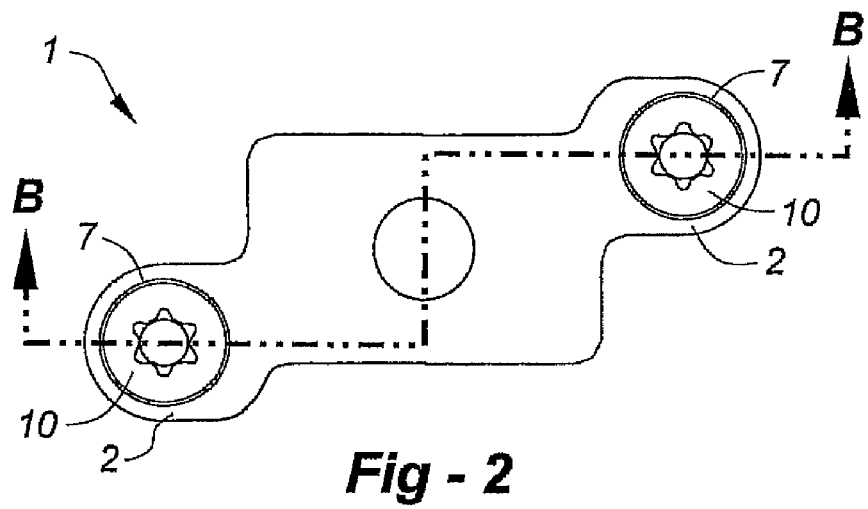
FIG. 2 provides a top view of the implant with the fasteners in place in the fastener-retaining portion of the implant.
Figure 3:
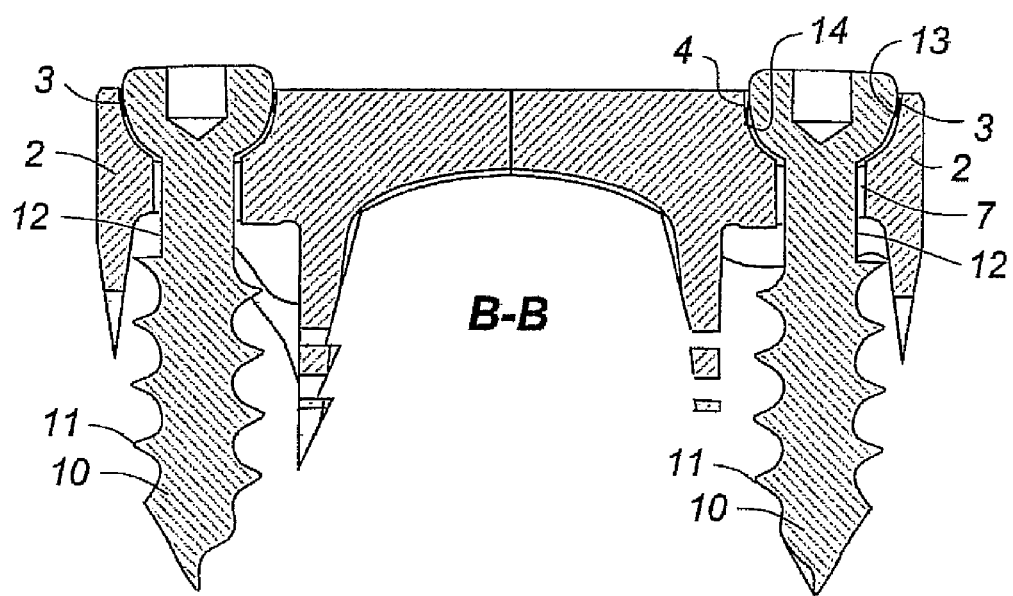
FIG. 3 shows a cross section of the implant and fastener or screw.

FIG. 2 provides a top view of the implant (1) with the fasteners (10) in place in the fastener-retaining portion (2) of the implant. FIG. 3 shows a cross section of the implant (1) and fastener or screw (10). The cross section shows the fasteners (10) with one of the protrusions (14) and the screw thread (11). Hole (7) is pre-tapped or self-tapped by the fastener (10). The screw thread relief (12) is shown after being fully screwed into the bone (not shown) such that the fastener contact surface (13) and implant contact surface (3) are in contact. Protrusions (14) on the fastener engaged recesses (4) in the implant (1), preventing the fastener (10) from rotating and backing-out. Those of skill will recognize that the placement of the protrusions and recesses may be reversed.

Figure 4:
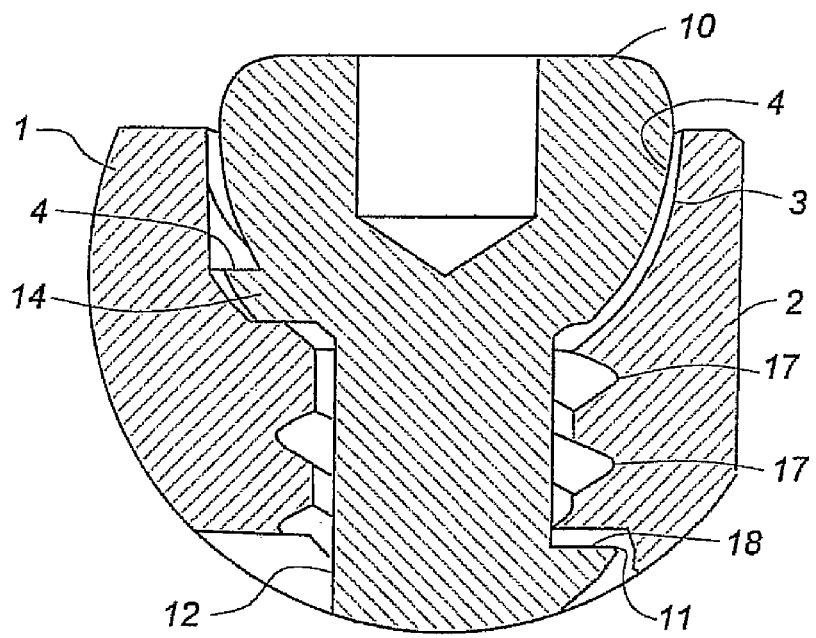
FIG. 4 is a close-up cross-sectional view of the implant and fastener head showing internal threads and fastener protrusions engaged with implant recesses, preventing the fastener from backing out.

FIG. 4 is a close-up, cross-sectional view of the implant (1) and fastener head (10), showing internal thread (17) with fastener protrusions (14) engaged with implant recesses (4) preventing the fastener (10) from rotating in the reverse (loosening) direction. As discussed above, the internal thread (17) was pre-tapped or partially pre-tapped. Alternatively, the fastener (10) could tap all or a portion of the internal threads (17) as it is rotated into place.

Land (18) is shown at the intersection of the screw thread (11) and the relief (12). The relief (12) allows rotation of the screw, while land (18) retains the fastener (10) from disengaging from the implant (1). Should a fastener (10) pullout of the bone; it will be retained by interference between the land (18) on the screw thread (11) and the internal thread(s) (17). Thus, the implant (1) is held in place by other fastener(s) (10), such that every fastener (10) must pull out and the implant (1) disengage for the implant (1) to dislodge. The land (18) also assures that the fastener protrusions (14) and implant recesses (4) do not disengaged should the screw strip out of the bone, eliminating the engagement force being applied by the bone.

The invention includes novel methods for implanting and providing tactile feedback to the surgeon that the fastener is tight and has been installed. Tactile feedback is often key to minimally invasive surgical procedures. Endoscopic surgery by its nature prevents the surgeon from having direct visual and tactile contact with the tissue. Such procedures are executed using instruments with long, slender shafts adapted to enter the body cavity through small incisions. This distance limits the ability of the surgeon to have a tactile "feel" for what is happening.

The method of installation includes the steps of providing a spinal implant with anti-rotation features, one or more fasteners for fastening the implant to a bone where each fastener also has corresponding anti-rotation features, and a relief in the fastener screw thread such that when the thread reaches the relief, it disengages the implant. This allows the fastener to turn without axial translation with respect to the implant while retaining the screw in the implant.

The method also includes installing the fastener using anti-rotational features such that torque related tactile feedback is communicated to the surgeon. Tactile feedback assures that a bone screw is adequately tightened and that the fastener retention features are fully engaged.

The implant is placed on a vertebral body or other bony surface and fastener(s) are inserted through the fastener retaining hole(s). As each fastener is rotated the helical thread taps the fastener-retaining hole if it is not pre-tapped and also enters the bone. As the head of the fastener approaches the fully down position, the screw thread disengages from the internal threaded section of the fastener retain hole such that it can turn freely. This allows the fastener to turn independently of the implant and to pull the implant down as the fastener continues to rotate into the bone.

As the fastener engages the surface of the implant the protrusions engage the recesses and start to provide limited feedback in the form of increasing and rapidly decreasing torque to tighten the fastener. As the fastener gets tighter the feedback will increase in intensity. If the direction of the rotation is reversed, the anti-backout surfaces on the recesses will engage similar surfaces on the protrusions. Engagement of these surfaces will prevent the fastener from backing out. In the event the fastener must be removed, a high torque may be applied to overcome the features. The land on the thread will prevent the fastener from dislodging from the implant should it strip out of the bone. Only a catastrophic failure where every fastener strips out and other retentions means fail (such as barbed legs of a staple) would allow the implant to dislodge.

Unique to the invention, the fastener is placed and the anti-backout features are activated without a secondary step. Locking mechanisms such as cover plates require a secondary operation for each fastener or group of fasteners. Such mechanisms require additional parts, add cost, and reduce reliability when compared to the current invention where the mechanism is totally within features on the implant and fastener.

The inventive system is fully compatible with standard instrumentation and method. The features do not have components that protrude significantly or unusually beyond the shape of a traditional bone screw. Other types of fastener-retention systems such as locks and mechanisms require space for moving or sliding parts and can protrude outside the normal configuration required for a bone screw. Slides and snap rings require space for movement that is valuable for strength of the implant and restrict the potential to make the implant slim for good visibility during placement. It is likely that specially designed screwdrivers and placement tools would need to be larger for screws that have collars or snap rings or where the screwdriver must avoid mechanism located on or as a part of the implant. Although the invention includes recesses with low-profile protrusions, such features do not preclude the use of current instruments know in the art. Such instruments allow for good visibility and no retraining of surgeons and support staff. Once placed the fastener and implant may be removed by applying high torque to the fastener to overcome the anti-rotational features.

I claim:

1. An orthopaedic implant, comprising
   a body having a top surface and a bottom surface;
   a fastener-receiving bore extending through the body, the bore including a threaded lower portion and a flared wall at the top surface of the body, the flared wall having a smooth surface with the exception of a plurality of recesses spaced apart peripherally around the flared wall;
   a fastener having an end with threads that match the threaded lower portion of the body and a head with an outer surface corresponding to the flared wall of the bore in the body, the outer surface of the head being smooth with the exception of one or more projections, each projection being dimensioned to engage with one of the recesses such that when the fastener is inserted through the bore and tightened into a bone, the protrusions and recesses ultimately interlock to minimize or prevent back-out of the fastener from the body; and
   wherein the fastener further includes a relief between the head and the threaded end creating a land that allows rotation of the fastener but prevents pull-out due to interference with the bottom surface of the body.

2. The implant of claim 1, wherein the fastener self-taps the lower portion of the body as the fastener is advanced.

3. The implant of claim 1, wherein the bottom surface of the body includes one or more bone-engaging legs, spikes or barbs.

4. The implant of claim 1, wherein the body is a cervical plate.

5. The implant of claim 1, wherein:
   the body is an elongate plate defining an axis; and
   the bore is off-axis.

6. The implant of claim 1, wherein:
   the body is an elongate plate defining an axis including two bores; and
   both bores are off-axis.

7. The orthopaedic implant of claim 1, wherein:
   the flared wall in the body forms a concave, cup-shaped receptacle; and
   the outer surface of the head forms a rounded convex shape.

8. The orthopaedic implant of claim 1, wherein the flared wall in the body and the outer surface of the head are both hemispherical.

9. The orthopaedic implant of claim 1, wherein the flared wall in the body and the outer surface of the head respectively include the same number of equally spaced-apart projections and recesses.

10. The orthopaedic implant of claim 1, wherein the projections and recesses each include a ramp-like surface and a stop surface.

* * * * *